United States Patent [19]

Shillito et al.

[11] Patent Number: 4,999,299
[45] Date of Patent: Mar. 12, 1991

[54] PROPAGATION PROCESS EMPLOYING AGAROSE MEDIUM

[75] Inventors: Raymond D. Shillito, Rheinfelden; Jerzy Paszkowski, Riehen; Ingo Potrykus, Magden, all of Switzerland

[73] Assignee: Ciba-Geigy Corporation, Ardsley, N.Y.

[21] Appl. No.: 205,025

[22] Filed: Jun. 3, 1988

Related U.S. Application Data

[63] Continuation of Ser. No. 53,582, May 18, 1987, abandoned, which is a continuation of Ser. No. 801,375, Nov. 22, 1985, abandoned, which is a continuation of Ser. No. 601,876, Apr. 19, 1984, abandoned.

[30] Foreign Application Priority Data

Apr. 29, 1983 [CH] Switzerland .................. 2317/83

[51] Int. Cl.$^5$ .................................. C12N 5/04
[52] U.S. Cl. ........................ 435/240.47; 435/240.4; 435/240.48; 435/240.49; 435/240.54; 47/DIG. 11
[58] Field of Search ................ 935/94, 98, 67; 435/240.48, 240.49, 240.5, 240.21

[56] References Cited

U.S. PATENT DOCUMENTS 3,514,900  6/1970  McDade ................. 47/58
4,217,730  8/1980  Abo El-Nil ............. 47/58
4,338,745  7/1982  Misawa et al. .......... 47/58
4,473,648  9/1984  Tang ................... 435/240

OTHER PUBLICATIONS

Maramorosch et al; *Practical Tissue Culture Applications*, Academic Press, N.Y., 1979, pp. 31–34.
Reinert et al., *Plant Cell and Tissue Culture*; Springer-Verlag, N.Y., 1982, pp. 40–45.
Singleton et al., *Dictionary of Microbiology*; John Wiley & Sons, New York; © 1978; p. 7.
Staba, E. John; *Plant Tissue Culture as a Source of Biochemicals;* CRC Press Inc., Boca Raton, Fla., © 1980; pp. 100–102.

*Primary Examiner*—Jacqueline Stone
*Assistant Examiner*—Marian C. Knode
*Attorney, Agent, or Firm*—Steven R. Lazar; JoAnn Villamizar

[57] ABSTRACT

The invention describes a process for culturing proliferating aggregates of plant cells, which comprises (a) uniformly plating isolated protoplasts, or isolated cells regenerated from protoplasts, in or on an agarose-solidified culture medium, and/or (b) cutting this pretreated and solidified culture medium into segments, transferring said segments to a liquid nutrient solution and continuing culturing in both cases until the cell aggregates have attained the desired size.

14 Claims, No Drawings

PROPAGATION PROCESS EMPLOYING AGAROSE MEDIUM

This application is a continuation of application Ser. No. 053,582, filed May 18, 1987 which is a continuation of application Ser. No. 801,375, filed Nov. 22, 1985, which is a continuation of application Ser. No. 601,876, filed Apr. 19, 1984, all now abandoned.

The present invention relates to the process described hereinafter for culturing or propagating plant cells formed from protoplasts using agarose in the culture medium.

Owing to the rapid increase in world population, the breeding of useful plants is a major point of focus of biological research. On the one hand there is the search for alternative reproducible sources of food, energy and raw materials, e.g. new plant species, especially hybrid species with valuable properties such as increased resistance to pathogens (e.g. phytopathogenic insects, fungi, bacteria, viruses etc.), to atmospheric influences or location conditions (e.g. heat, cold, wind, soil condition, moisture, dryness etc.), or with increased formation of reserve or storage substances in leaves, seeds, tubers, roots, stalks etc. On the other hand, in addition to the growing need for valuable biomass, there is also an increased need for pharmaceutically acceptable active ingredients of plant origin and derivatives thereof, e.g. alkaloids, steroids and the like, which, because of the low yield from natural sources, are being increasingly made available by alternative methods, for example by extraction from genetically manipulated plant species.

Accordingly, there is growing interest in the practical possibility of selectively manipulating numerous plant species.

It is common knowledge that isolated totipotent cells of higher plants, in or on polymer-containing culture media, can be induced to produce embryonic cell aggregates and, in some cases, viable and reproducible plants. However, as the relatively solid cell walls normally constitute an almost insuperable barrier to manipulations such as cell fusions or gene transplants, it is advantageous to use in these cases the naked protoplasts which are obtained from the corresponding totipotent intact cells by removing the cell walls by methods known per se with the aid of enzymes (pectinases, cellulases etc.).

Up to now agar has been commonly used as the gelling agent for culturing plant cells and, in particular cases, also protoplasts. However, agar is toxic to most protoplast types and only a few exceptional cases are known in which it is possible to culture particularly robust protoplasts successfully in agar.

For this reason, the search began recently to find other useful culture media. Among other things, it was found that alginate and agar have equally good plating properties. [Adaoha-Mbanaso E. N., Roscoe, D. H. (1982), *Plant Sci. Let.* 25: 61-66].

Agarose has been used up to now exclusively for culturing animal cells and micro-organisms. However, culturing plant cells poses a very different set of problems on account of the entirely different physiology. Techniques of animal cell culture cannot in the nature of things be applied to the proliferation of plant cells or to the formation of cell aggregates from plant protoplasts.

It is therefore the object of the present invention to avoid the difficulties arising out of the use of agar or purified agar for growing cell cultures formed from plant protoplasts, and to provide a general process which is applicable not only to particularly robust, but to all protoplast types, by means of which process it is possible to culture cell aggregates or embryonic plants while avoiding the phytotoxic effects of the culture medium. This object is achieved in a surprising manner by the process of this invention.

Agarose is one of the constituents of agar. Commercially available agar consists mainly of a mixture of neutral agarose and ionic agaropectin with a large number of attached side groups. Commercial agarose is obtained from agar by conventional commercial methods.

Usually a number of side chains remain intact and determine the physiochemical properties such as gel formation and melting temperature.

Agarose which melts and gels at low temperature is obtained e.g. by subsequently introducing hydroxyethyl groups into the agarose molecule. Agarose modified in this manner shall be referred to throughout this specification as LMT (low-melting) agarose.

Surprisingly, it has now been found that the difficulties arising out of the proliferation of plant cells formed from protoplasts in agar, in particular the high mortality of the protoplasts, are very substantially diminished, or even entirely eliminated, by using agarose instead of agar. The proliferation of the cells formed from the protoplasts can be still further stimulated by using not only a culture medium solidified with agarose, especially with LMT agarose, but additionally by cutting the solidified culture medium on which the protoplasts are plated into smaller segments, and incubating said segments, individually or in groups, in a nutrient solution until cell aggregates of the desired size have formed.

It was entirely unexpected that the use of any agarose would be able significantly to promote the ability to form cell cultures from different protoplast types, in particular from sensitive protoplasts, so that protoplast types which it has so far not been possible to culture can now also be stimulated to form cell aggregates right through to whole plants.

Accordingly, the present invention relates to a process for culturing proliferating aggregates of plant cells, which comprises (a) uniformly plating isolated protoplasts, or isolated cells regenerated from protoplasts, in or on an agarose-solidified culture medium, and/or (b) cutting this pretreated and solidified culture medium into segments, transferring said segments to a liquid nutrient solution and continuing culturing in both cases until the cell aggregates have attained the desired size.

The term "cell aggregate" used throughout this specification will be understood as meaning cultures consisting of a computable number of plant cells right through to complete plants.

A particularly preferred embodiment of the invention is a process for culturing proliferating aggregates of plant cells, which comprises (a) uniformly plating isolated protoplasts, in or on an agarose-solidified culture medium, and/or (b) cutting this pretreated and solidified culture medium into segments, culturing said segments in 1 to 10,000, preferably 5 to 10,000 and, most preferably 20 to 100, times their own volume of a liquid nutrient solution suitable for culturing plant cells, and continuing culturing in both cases in the temperature range from 0° to 40° C. until the cell cultures have reached the desired size.

A particularly advantageous temperature range for culturing the cell aggregates is from 12° to 30° C.

Of pre-eminent interest is the technical and commercial breeding of plants from protoplasts.

The novel process of this invention conveniently comprises the steps of modifying the plate culturing method conventionally employed for replicating microorganisms such that the protoplasts, which have been isolated, sterilized and purified in known manner, are taken up in a culture medium solidified with agarose instead of in agar, and carrying out the steps of plating the protoplasts in said medium, cutting the agarose-solidified culture medium in which the protoplasts are embedded into smaller, preferably similar, segments, transferring said segments, individually or together, to a container which is partially filled with a suitable nutrient solution, and subjecting said container to constant shaking in the indicated temperature range, in the dark or under light conditions, until cell aggregates or embryonic viable plants of the desired size have formed.

The agarose segments in which the cell aggregates are embedded are most suitable for large-scale culturing in bioreactors in order to obtain valuable natural products.

Embryonic plantlets can be grown to mature plants, e.g. hybrid plants, with particularly valuable properties, and further reproduced by conventional biological methods.

The term "segment" in the context of this invention denotes a three-dimensional irregular or, preferably, regular structure, e.g. discs, spheres, cubes, prisms, cones and the like, having an average cross-section of 1 to about 100 mm, preferably 2 to 60 mm, and most preferably, 2 to 10 mm. Spherical segments of average diameter are particularly suitable for the large-scale culturing of cell aggregates in fermentors.

The process of this invention is more efficient than all known ones, especially for producing cell colonies and subsequently cultures from recalcitrant or problem protoplasts. It is distinguished by its simplicity and can be used for culturing protoplasts of different origin and for fused as well as genetically manipulated protoplasts. The process is suitable for selectively culturing plant cells with one or more of the advantageous properties described above. Further, it can also be used for culturing plant cells from protoplasts obtained from tumour tissue.

Accordingly, the use of agarose for culturing plant cells or plant colonies is an essential feature of this invention. Furthermore, it is immaterial which type of agarose is used, as different agaroses differ only in degree with respect to their use in the process of this invention and are altogether superior to agar for culturing plant cell colonies from protoplasts.

Although the experimental results of Examples 1 to 6 demonstrate unequivocally that agarose is far superior to agar for culturing plant cells from protoplasts, a certain problem does also arise in practice when using agarose. Thus it is sometimes found that that the cell aggregates in the process of formation suffer growth arrest at an advanced stage of development or even die. The cause of growth arrest may be a kind of exhaustion of the nutrient solution, while cell death may result from an increase in toxic substances released by the developing cell aggregates. Surprisingly, however, both undesirable effects can be eliminated by simple means. Unhindered growth of the cell aggregates is observed if the primary agarose-solidified medium on which the protoplasts are plated is cut into smaller segments which are desirably of the same size or same shape, and these segments are then transferred to e.g. a shaking container which preferably contains a substantial volume of a suitable liquid nutrient solution. Depending on the protoplast type, it can be advantageous if the segmentation of the agarose-solidified culture medium is effected 0 to 7 days, usually 3 to 4 days, after plating the protoplasts. The best time for petunia protoplasts is the 4th day, for tobacco and *Crepis capillaris* the 3rd day, after plating. When plating *Brassica rapa* protoplasts, segmentation is most preferably effected immediately after gelation of the agarose.

In addition to the use of agarose as gelling agent for culture media, cutting the agarose-solidified culture medium in which the protoplasts are embedded into suitable segments also constitutes an important object of this invention. Further objects of the invention are also the cell aggregates and/or plants produced by the process described above.

To accelerate cell growth, the nutrient solutions employed in the process of the invention may also contain traces of organic compounds, e.g. vitamins, carbon donors such as cane sugar and glucose, phytohormones such as auxins and cytokinins, and natural extracts such as malt extracts or coconut milk and, if necessary, other useful ingredients. The culture or incubation conditions, e.g. temperature of the nutrient, the action of light and duration of the incubation or culturing, can be adapted to the respective conditions such as plant species and protoplast type or the scale of the experiment.

The culturing of useful protoplasts is described below in Preparatory Examples (a) to (c). In these Examples, the starting cell culture can originate from any organ or tissue of the plant, e.g. roots, stalks, leaves, blossoms, seeds, pollen etc., e.g. also from callus cultures. The techniques of culturing protoplasts are generally known and are not limited to the species indicated in Examples (a) to (c).

PREPARATORY EXAMPLES FOR CULTURING PURE PROTOPLASTS

EXAMPLE (A)

To culture protoplasts, cell suspension cultures, prepared in a manner known per se, of the auxotrophic cell lines of the species *Hyoscyamus muticus* are treated with a solution of 4% w/v Cellulase Onozuka R.10 (available from Yakult Co. Ltd., Japan), 2% w/v Driselase (available from Chemische Fabrik Schweizerhalle, Switzerland), in 0.25M sorbitol, 0.025M $CaCl_2.2H_2O$, 0.5% w/v of, 2-(n-morpholino)ethanesulfonic acid (MES) (pH 5.2). The mixture is incubated overnight at 26° C., then filtered through a 100 μm steel mesh and the filtrate is diluted with the same volume of a 0.6M sucrose solution. The dilute filtrate is covered with an overlay solution of 0.16M $CaCl_2.2H_2O$ and 0.5% w/v of MES (pH 5.6). The protoplasts are collected from the interface of the layers, washed twice with the overlay medium and cultured in the complete medium B1 of Gebhardt et al. [(1981) Planta 153:81–89]. Medium B1 is designated below as nutrient medium A.

EXAMPLE (B)

Protoplasts of *Nicotiana tabacum*, line VR2

(Leaf protoplasts were isolated from 4–6 week old shoot cultures as described by Wullens et al, *Theor. Appl. Genet.*, 56 (1980) p.203–208 and cultured in K3 medium (Nagy and Maliga, Z. Pflanzenphysiol, 78 (1976) p.453-455) at a density of 50,000 cells per ml.) Shillito et al (1981) Mutat. Res. 81:165-175. The procedure for purifying these protoplasts is modified in that, following incubation in the enzyme solution, one half volume of 0.6M sucrose solution is added and the dilute mixture is covered as in Example (a) with an overlay solution of calcium chloride, the protoplasts are collected at the interface and washed with the same calcium chloride solution. The further procedure as described in Example (a) is repeated and the protoplasts are cultured in medium K3 (designated below as culture medium (B)).

EXAMPLE (C)

Isolation of protoplasts of two Petunia hybrida lines of haploid "Mitchell" (PMB Newsletter, 1980), obtained from M. Hanson, Charlottesville, Va., U.S.A., and the a mutant of Petunia hybride var. Blue Bedded (Potrykus I (1970), Z. Pflanzenzuchtung 63:24-40). Young, fully expanded leaves are sterilised with a solution of 0.01% w/v of $HgCl_2$ and 3 drops of Tween 80 per 100 ml and washed 5 times with sterile distilled water. Leaf halves without mid-ribs are stacked in piles of 6 and wetted with an osmoticum (0.375M mannitol, 0.05M $CaCl_2$, 0.5% w/v of MES; pH 5.8) and cut into thin sections 0.5 mm wide. The sections are vacuum infiltrated with the enzyme solution (0.2% w/v of Cellulase Onozoka R.10, 0.2% w/v of Macerozyme; pH 5.6 in the osmoticum. After incubation overnight at 12° C. in the dark, one volume of the above osmoticum is added and the mixture is filtered through a 100 μm mesh. The protoplasts are washed twice with the osmoticum and overlayered on 0.6M sucrose to remove débris. The protoplasts from the interface are washed once more with the osmoticum and incubated in a culture medium (DPD:Durant et al., (1973), Z. Pflanzenphysiol, 69:26-34) for 12 hours per day in the dark at 26° C.

The results reported below of the comparative tests demonstrate convincingly the surprising advantageous effects observed (a) by substituting agarose for agar and (b) by cutting the agarose-solidified culture media and putting this into a shaken liquid culture when culturing plant cell aggregates from protoplasts.

EXAMPLES OF COMPARATIVE TESTS OF AGAR AND AGAROSE AS CULTURE MEDIUM (α) All nutrient solutions are sterilised by ultrafiltration through 0.22 μm Nalgene filters. Solidified media are prepared by mixing equal volumes of double concentrated nutrient solution with double concentrated and autoclaved gelling agent.

Suitable liquid nutrient solutions are e.g. the media listed below as A, B, C, D and E:

(A) complete medium B1: Gebhardt et al., Planta, 153, 81-89 (1981)
(B) K3 medium: Nagy and Maliga, Z. Pflanzenphysiologie 78, 453-455 (1976)
(C) DPD medium: Durand et al., Z. Pflanzenphysiologie 69, 26-34 (1973)
(D) medium of Lindsmaier, E. M. and Skoog, F., Physiologia Plantarum 18, 100-127 (1965)
(E) medium of Nitsch, J. P. and Nitsch, C., Science 163, 85-87 (1969).

The gelling agents employed are:

(1) Agarose: SEA PLAQUE LMT ® (Marine Colloids) in all tests. [Only in the tests reported on in Example 5 are other agaroses specified therein employed].

(2) Agar: Difco Bacto-agar in all tests.
(3) Purified agar: 454 g of agar (as in (2) above) is washed in succession with 10 liters of water, 5 liters of acetone and 5 liters of ethanol and dried in vacuo at 40° C. A white odourless powder is obtained.

The protoplasts obtained in Examples (a) to (c) are plated by the conventional plate culturing method in petri dishes in thin layers on the gelling and purified culture media. Agar or agarose is used in a concentration of 0.4% w/v, except where otherwise specified. A total of 3 ml or 10 ml of medium is used per 6 cm or 9 cm petri dish respectively.

For experiments in which agar or agarose segments are used, the protoplasts are uniformly plated in the medium before it is segmented. The segments are then put into 30 ml of nutrient solution in containers of 10 cm diameter and incubated on a gyrotatory shaker at 26° C. in the dark or in light. The liquid culture medium is replaced at regular intervals or continuously. Microscopic evaluation of the usefulness of the method and of the advantageous influence on the formation of cell colonies from protoplasts is made after incubation for 4 to 6 weks by counting and inspecting the cell aggregates on a representative number of frames. In the segmentation experiments, the dishes containing the segments floating in the nutrient solution are photographed at 14 day intervals and the number and size of the cell aggregates visible in the segments are assessed.

(β) Test Results

Example 1: Number of cell colonies recovered from plating $10^5$ cells or protoplasts of the species Hyoscyamus muticus, line VIII B9 (trp⁻) in 10 ml of solidified medium (B).

| Solidified medium (B) | Cells | Protoplasts |
|---|---|---|
| 0.4% agar | 20 | 0 |
| 0.4% agarose | not tested | 1102 |
| 0.8% agarose | 1024 | 472 |
| without gelling agent | 1000 | 120 |

The results of Example 1 show that agarose is more suitable than agar both for culturing cells and for culturing cells from protoplasts, and that agar is toxic to the protoplasts and cells used in this experiment. Density/ml will be understood here and in the subsequent Examples as meaning the number of protoplasts or cells per ml of culture medium.

Example 2: Plating efficiency (%) of tobacco (VR2) protoplasts with increasing dilution in medium B

| solidified medium (B) | Density/ml | | | |
|---|---|---|---|---|
| | 6000 | 3000 | 1000 | 300 |
| agarose | lawn* | 4.3 | 2.2 | 0.22 |
| agar | lawn* | 1.9 | 0 | 0 |
| without gelling agent | lawn* | 1.3 | 0 | 0 |

*Lawn of cells too dense to count

As can be seen from the results of Example 2, tobacco (VR2) protoplasts form cell aggregates in agar at high density. With increasing dilution, the positive influence of agarose on the development of cell colonies is greater.

Better growth using small concentrations of protoplasts is also confirmed by the results of Example 3 for protoplasts of the species Hyoscyamus muticus (VA5, his⁻), both in purified agar and in the liquid phase (nutrient solution A) without gelling agent.

Example 3: Plating efficiency (%) of *Hyoscyamus muticus* (VA5, his⁻) protoplasts with increasing dilution in medium A

| solidified medium (A) | Density/ml | | | |
|---|---|---|---|---|
| | 11 000 | 3700 | 1300 | 600 |
| agarose | lawn* | 9.5 | 3.2 | 0.25 |
| purified agar | 0.25 | 0.2 | 0 | 0 |
| without gelling agent | 0.06 | 0 | 0 | 0 |

*Lawn of cells too dense to count

As the following Example 4 using protoplasts of the species *Hyoscyamus muticus* (VIII B9 trp.⁻) clearly demonstrates, the toxic effects of agar stems at least partly from diffusible substances, as both agar and purified agar inhibit cell growth in the agarose upper layer.

Example 4: Number of cell colonies formed after plating protoplasts of the species *Hyoscyamus muticus* (VIII B9 trp⁻) in a thin layer of agarose-solidified medium A with a lower layer of agarose or purified agar or agar, or in unsolidified nutrient solution (total volume: 3 ml).

| | Number of Propoplasts/ml | | | |
|---|---|---|---|---|
| | 50 000 | | 10 000 | |
| solidified medium (A) | upper layer | | | |
| | identical | agarose | identical | agarose |
| agarose | 215 | 221 | 66 | 68 |
| purified agar | 0 | 0 | 1 | 2 |
| agar | 0 | 0 | 0 | 0 |
| without gelling agent | 48* | | 3.3* | |

*liquid controls

Example 5 demonstrates the suitability of different types of agarose for culturing protoplasts of the species *Hyoscyamus muticus* and tobacco (VR2) at high and low densities. Purified agar and agar are ranked last, whereas SEA PLAQUE ®, LMT and BRL-LMP ® agaroses have similar characteristics and are much superior to any of the other agaroses tested. Purified agar and agar are much poorer than all other agaroses tested and tend in general to inhibit the development of protoplasts.

| Agarose type | Characteristics | | | Manufacturer |
|---|---|---|---|---|
| | sulphate % | *EEO (−m_r) | Approx. dynamic gelling temperature °C. | |
| SEAPLAQUE ® LMT (FMC) | ≦0.15 | ≦0.15 | 20–30 | Marine Colloids |
| LMP ® (BRL) | ≦0.15 | ≦0.15 | <30.0 | Bethesda Research Labs |
| TYPE VII ® (Sigma) | ≦0.15 | ≦0.15 | <30.0 | Sigma |
| HGT ® (Sigma) | ≦0.3 | ≦0.1 | 42.0 | Sigma |
| HGTP ® (FMC) | ≦0.1 | ≦0.1 | 42.0 | Marine Colloids |
| HGT ® (FMC) | ≦0.30 | ≦0.1 | 42.0 | Marine Colloids |
| LE ® (FMC) | ≦0.35 | ≦0.15 | 36.0 | Marine Colloids |
| STANDARD LMT ® (BioRad) | ≦0.05 | ≦0.1 | <37.0 | BioRad |
| SEAPREP ® (FMC) | ≦0.1 | ≦0.05 | 8–17 | Marine Colloids |

*EEO: Electro endosmosis

All experiments are carried out at 0.8% and 0.4% w/v, where a gel will form at these concentrations. Sea Prep forms a gel only above 0.8% w/v.

The influence on the formation of cell cultures after cutting a solidified culture medium embedded with protoplasts and culturing this in a liquid medium was investigated using haploid "Mitchell" petunia protoplasts. Agar, purified agar and agarose were used as gelling agents for the culture medium. The growth of cell aggregates in the segments and in plates was compared with that obtained with the conventional plating method in petri dishes. As the results of Example 6 show, the number of cell colonies formed from protoplasts in the segments was always greater than in the conventional plates that were not transferred to liquid. In all cases investigated, the culture of protoplasts in agarose segments in liqluid medium results in the most efficient growth of cell aggregates.

Example 6: Comparative investigation of the development of cell aggregates in solid media by the conventional plating method and in segments in a nutrient solution. Percentage growth of cell colonies of haploid *Petunia hybrida* "Mitchell" formed from protoplasts after 2 weeks in a solid medium either cut into segments and shaken in the nutrient solution* or left in the petri dishes uncut.

| Dichte/ml: | $8 \times 10^4$ | | $4 \times 10^4$ | | $2 \times 10^4$ | | |
|---|---|---|---|---|---|---|---|
| Method: | Dish | Segment | Dish | Segment | Dish | Segment | |
| agarose | 14.8 | 22.8 | 26.0 | 31.2 | 27.2 | 52.4 | |
| purified agar | 3.2 | 14.2 | 6.2 | 8.4 | 7.4 | 10.6 | [%] |
| agar | 2.6 | 5.4 | 2.2 | 3.2 | 0.12 | 0.81 | |

*nutrient solution (C)

The experiment demonstrates unequivocally the superiority of the use of agarose pieces in a liquid medium as compared with purified agar and agar, both in dishes and in segments.

Similar results are obtained e.g. with protoplasts of the species *Crepis capillaris*, a mutant of *Petunia hybrida* was Blue Bedder, *Brassica rapa*, *Lycopersicon esculentum*, and *Nicotiana tabacum*.

EXAMPLE 7

Regeneration of Plants from Protoplasts of the Species *Nicotiana tabacum*

About $5 \times 10^4$ protoplasts per ml of the species *Nicotiana tabacum* are plated in a culture medium B [K3 medium] solidified with 1% w/v of agarose and cultured for 10 days in sealed petri dishes in a climatic chamber (3000 lux; 24° C.; about 100% relative humidity). This solid medium is then cut into segments of equal size (diameter 1 cm). These segments are put into 10 times their volume of a nutrient solution B modified with 0.25M sucrose, 0.05 mg/l of 2,4-dichlorophenoxyacetic acid, 0.1 mg/l of 6-benzylaminopurine and 0.1 mg/l of kinetin, and uniformly shaken in this medium. The medium B is replaced after one week, the sucrose content being reduced to 0.2M. The segments in the liquid culture are shaken for a further 4 weeks, with the medium being replaced each week. The cell colonies which have formed are transferred to an agarose-solidified medium D with 0.2M of sucrose, 0.05 mg/l of 2,4-dichlorophenoxyacetic acid, 2 mg/l of 2-naphthylacetic acid and 0.1 mg/l of kinetin. After 4 weeks the callus formed cultures are transferred to an agarose-solidified medium D with 0.2 mg/l of 6-benzylaminopurine, in which shoots form. These shoots are transferred to an agarose-solidified medium E and, after rooting, are transplanted in soil and grown to mature plants.

What is claimed is:

1. A process for culturing plant cell aggregates to form calli or plantlets which comprises:
    (a) uniformly plating isolated protoplasts in a solidified culture medium, the solidifying component of which is agarose in the absence of agaropectin,
    (b) incubating segments of the solidified culture medium, which segments contain the protoplasts, in a liquid nutrient solution until the protoplasts form plant cell aggregates, and
    (c) culturing the plant cell aggregates under conditions sufficient for the formation of calli or plantlets until the plant cell aggregates have reached a callus or plantlet stage.

2. A process according to claim 1, which comprises transferring the segments into 1 to 10,000 times their volume of a liquid nutrient solution suitable for culturing plant cells, and continuation of culturing in the temperature range from 0° to 40° C.

3. A process according to claim 1, wherein the incubation step of the process occurs at an incubation temperature in the range of from about 12° to about 30° C.

4. A process according to claim 2, wherein the segments are put into 5 to 10,000 times their own volume of a nutrient solution suitable for culturing plant cells.

5. A process according to claim 4, wherein the segments are put into 20 to 100 times their own volume of a nutrient solution suitable for culturing plant cells.

6. A process according to claim 1, wherein the solidified culture medium is incubated in the liquid nutrient solution not later than 7 days after plating with protoplasts.

7. A process according to claim 6, wherein segmentation is effected 3 to 4 days after plating.

8. A process according to claim 1, which comprises the use of segments of equal size and regular shape and having an average diameter of 1 to about 100 mm.

9. A process according to claim 8, which comprises the use of segments having an average diameter of 2 to 60 mm.

10. A process according to claim 9, wherein the segments are discs, spheres, cubes, prisms or cones having an average diameter of 2 to 10 mm.

11. A process according to claim 1, which comprises the use of protoplasts which are isolated from a plant of a species selected from the group consisting of *Nicotiana tabacum, Hyoscyamus muticus, Lycopersicon esculentum, Crepis capillaris, Brassica rapa*, and *Petunia hybrida*.

12. A process according to claim 1, wherein the solidifying agarose is selected from the group consisting of SEA PLAQUE LMT ®, LMP ®, TYPE VIII ®, HGT ®, HGTP ®, LE ®, STANDARD LMT ® and SEA PREP ® agarose.

13. A process for culturing plant cell aggregates from plant cells formed from protoplasts to form calli or plantlets, which comprises:
    (a) culturing protoplasts under conditions in which the protoplasts regenerate cell walls to form plant cells;
    (b) plating the plant cells formed from protoplasts in a solidified culture medium, the solidifying component of which is agarose in the absence of agaropectin;
    (c) incubating segments of the solidified culture medium, which segments contain the plant cells, in a liquid nutrient solution until the plant cells form plant cell aggregates; and
    (d) culturing the plant cell aggregates under conditions sufficient for the formation of calli or plantlets until the plant cell aggregates have reached a callus or plantlet stage.

14. A process according to claim 13, wherein the solidified culture medium is incubated in the liquid nutrient solution not later than 7 days after the plant cells are cultured to form protoplasts.

* * * * *